United States Patent [19]
Fisher et al.

[11] Patent Number: 5,851,773
[45] Date of Patent: Dec. 22, 1998

[54] METHODS OF IDENTIFYING INDUCIBLE INHIBITORS OF TRANSFORMATION PROGRESSION

[75] Inventors: Paul B. Fisher, Scarsdale; Zao-zhong Su, New York, both of N.Y.

[73] Assignee: The Trustees of Columbia University in the City of New York, New York, N.Y.

[21] Appl. No.: 764,743

[22] Filed: Dec. 12, 1996

Related U.S. Application Data

[63] Continuation of Ser. No. 209,478, Mar. 10, 1994, abandoned.

[51] Int. Cl.⁶ .................................................. C12Q 1/68
[52] U.S. Cl. ................................................................ 435/6
[58] Field of Search ............................................... 435/5, 6

[56] References Cited

U.S. PATENT DOCUMENTS

| | | | |
|---|---|---|---|
| 4,910,132 | 3/1990 | Kinght et al. | 435/5 |
| 5,266,464 | 11/1993 | Housey | 435/29 |

OTHER PUBLICATIONS

Borner, C., et al. (1988), *Proc. Natl. Acad. Sci. USA* 85:2110–2114.
Borner, C., et al. (1991), Nature, 353:78–80.
Borner, C., et al. (1992a), *J. Biol. Chem.*, 267:12892–12899.
Borner, C., et al., (1992b), *J. Biol. Chem.*, 267:12900–12910.
Duigou, G.J., et al. (1989), *N.Y. Acad. Sci.*, 567:302–306.
Duigou, G.J., et al. (1990), *Mol. Cell. Biol.*, 10:2027–2034.
Duigou, G.J., et al. (1991), *Oncogene*, 6:1813–1824.
Reddy, P.G., et al. (1993), Chromosome and Genetic Analysis.
Methods in Molecular Genetics, Adolph, D.W. (ed). Academic Press, Orlando. Florida., vol. I, pp. 68–102.
Su, Z.–z, et al. (1990), *Mol. Carcinogenesis,* 3:309–318.
Su, Z.–z., et al. (1991), *Mol Carcinogenesis,* 4:328–337.
Su, Z.–z., et al. (1992), *Cell. Mol. Biol.* 38:27–39.
Choi et al., Molecular and Cellular Biology (1990), vol. 10: pp. 4650–4657.
Hoeben et al., J. of Viroilogy (1991), vol. 65(2): pp. 904–912.
Rimoldi et al., Cancer Research (19910, vol. 51(1): pp. 324–330.
Su et al., Proc. Am. Assoc. Cancer Res. Annu. Meet. (1993), vol. 34(0): p. 178.

*Primary Examiner*—Terry A. McKelvey
*Attorney, Agent, or Firm*—John P. White; Cooper & Dunham LLP

[57] ABSTRACT

This invention provides a method of isolating a progression suppressor gene which suppresses expression of a gene regulated by a long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and thereby cause a subpopulation of the cells to selectively suppress the expression of the long terminal repeat regulated protein kinase C $\beta_1$ gene; c) selecting cells which express the progression suppressor gene; d) isolating mRNA from the cells from step (c); e) comparing the mRNA so obtained with mRNA obtained from the uninduced transformed cells so as to identify mRNA only expressed by the cells from step (c); and f) isolating the gene encoding the mRNA in step e) so as to thereby identify the progression suppressor gene.

11 Claims, 7 Drawing Sheets

METHODS OF IDENTIFYING INDUCIBLE INHIBITORS OF TRANSFORMATION PROGRESSION

This is a continuation of application Ser. No. 08/209,478, filed Mar. 10, 1994, now abandoned.

The invention disclosed herein was made with Government support under NIH Grant No. CA35675 and CA43201 from the Department of Health and Human Services. Accordingly, the U.S. Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Protein kinase C (PKC) is a key component in signal transduction in eucaryotic cells and when specific PKC isoforms are over-expressed in immortal mammalian cells, they can induce transformation-associated properties. In the present study, applicants demonstrated that a cloned PKC $\beta_1$ gene can induce an enhanced expression of the transformed phenotype in type 5 adenovirus (Ad5)-transformed rat embryo (RE) cells (clone E11), a process termed transformation progression. E11 cells expressing the PKC $\beta_1$ gene, clone B1/PKC, produce PKC $\beta_1$ mRNA and display enhanced PKC enzymatic activity and binding of [$^3$H]-phorbol-12, 13-dibutyrate (PDBu) to cell surface phorbol ester receptors. B1/PKC cells grow with increased efficiency in agar in comparison with parental E11 cells, and anchorage-independence is further enhanced in both cell types by addition of the tumor promoting agent 12-0-tetradecanoyl-phorbol-13-acetate (TPA). A single-exposure of B1/PKC cells to 5-azacytidine (AZA), followed by growth in the absence of this demethylating agent, results in B1/PKC-AZA clones which display a stable reversion of the progression phenotype to that of the unprogressed parental E11 clone. Loss of the progression phenotype corresponds with a reduction in PKC $\beta_1$-induced biochemical and cellular changes. In contrast, progression-suppression does not involve an alteration in expression of the Ad5 transforming genes, E1A and E1B, or the endogenous PKCε gene. TPA cannot induce the progression phenotype in B1/PKC-AZA cells, but it can reversibly induce an increase in the transcriptional rate and steady-state mRNA levels of PKC $\beta_1$ and c-jun and it increases AP-1 DNA-binding. These results indicate that the PKC $\beta_1$ gene can serve as a transformation progression-inducing gene in rat embryo cells previously transformed by Ad5 and progression may be mediated by the inactivation by methylation of an AZA-sensitive "progression suppressor gene(s)". The suppression process in B1/PKC cells is independent of expression of the Ad5-transforming genes but correlates directly with the reduced expression of the transfected PKC $\beta_1$ gene in AZA-treated B1/PKC cells.

The carcinogenic process is a consequence of a series of sequential changes in the phenotype of a cell resulting in the acquisition of new properties or a further elaboration of transformation-associated traits by the evolving tumor cell (reviewed in Fisher, 1984; Nowell, 1986; Nicholson, 1987; Weinstein, 1988; Bishop, 1991). The mechanism underlying tumor cell progression remains to be defined. Possible factors contributing to transformation progression include: activation of cellular genes that promote the cancer cell phenotype, i.e., oncogenes; loss or inactivation of cellular genes which function as inhibitors of the cancer cell phenotype, i.e., tumor suppressor genes; and/or combinations of these genetic changes in the same tumor cell (reviewed in Weinberg, 1985; Bishop, 1987, 1991; Sager, 1989; Marshall, 1991). Previous studies indicate that transformation of secondary rat embryo cells by Ad5 is often a sequential process resulting in the acquisition of and further elaboration of specific phenotypes by the transformed cell (Fisher et al., 1979 a,b,c). Progression in the Ad5-transformation model is characterized by the development of enhanced anchorage-independence and tumorigenic potential (as indicated by reduced latency time for tumor formation in nude mice) by progressed cells (Babiss et al., 1985). The progression phenotype in Ad5-transformed rat embryo cells can be induced by selection for growth in agar or tumor formation in a nude mouse (Fisher et al., 1979a,b,c), referred to as spontaneous-progression, or by transfection with the Ha-ras (T24) oncogene, referred to as oncogene mediated-progression (Duigou et al., 1989).

Both spontaneous and oncogene mediated-progression are stable cellular traits that have remained undiminished in Ad5-transformed rat embryo cells even after >100-passages in monolayer cultures. However, a single-treatment with the demethylating agent 5-azacytidine (AZA) results in a reversion in transformation progression in the majority of treated cellular clones (Babiss et al., 1985; Duigou et al., 1989; Reddy et al., 1993). These observations, and additional gene expression studies (Duigou et al., 1991; Reddy et al., 1993), suggest that progression is a reversible process that may be affected by the state of methylation of putative progression suppressor cellular genes. AZA can also induce both C3H 10T 1/2 and 3T3 cells to differentiate into muscle, fat and cartilage (Taylor & Jones, 1979; Jones 1985). This AZA-induced determination process in C3H 10 1/2 cells correlates with a resistance to transformation by 3-methylcholanthrene (Harrington et al., 1988). Similarly, non-terminal differentiation in 3T3 T cells induces resistance to both UV irradiation and 4-nitroquinoline oxide (Scott et al., 1989). Non-terminal differentiation also induces SV40-transformed 3T3 cells to repress expression of the large T antigen and to revert to a non-transformed state (Scott et al., 1989). It is not presently known if the anticancer activities demonstrated by AZA-treated and non-terminally differentiated mouse cells is analogous to the progression suppression phenotype induced by AZA in Ad5-transformed RE cells.

The tumor promoting diterpene phorbol ester, TPA can enhance expression of the transformed phenotype in Ad5-transformed rat embryo cells (Fisher et al., 1979 a,b,c). Since the major cellular receptor for TPA is PKC, these results suggest that alterations in expression of this enzyme may contribute to the process of transformation progression. PKC is a multigene family of serine/threonine kinases that plays a pivotal role in regulating signal transduction processes in mammalian cells (Ohno et al., 1991; Nishizuka, 1992). Biochemical and molecular cloning studies indicate that the PKC family consists of at least ten subspecies, including the $Ca^{2+}$-dependent conventional PKCs (cPKC: α, β1, β2, γ) and the $Ca^{2+}$-independent novel PKCs (nPKC: Σ, δ, C, η/L, Θ, λ) (Coussens, et al., 1986; Knopf, et al., 1986; Ono, et al., 1986, 1987, 1988; Parker, et al., 1986; Housey, et al., 1987; Ohno, et al., 1988; Backer, et al., 1991; Osada, et al., 1990; Nishizuka, 1992). The retention of different PKC isoforms during evolution, the subtle differences in enzymatic properties and substrate specificities of the PKC isoforms and the different tissue distribution of the PKC isoforms suggests a potential role for specific PKC isoenzymes in regulating defined biological functions (Ohno, et al., 1991; Nishizuka, 1992). Although extensively investigated, the specific functions of the various PKC subtypes still remain to be established (Ohno, et al., 1991; Nishizuka, 1988, 1992). One approach to study the effects of the various PKC isoforms on cellular physiology, although perhaps somewhat artificial because of the high levels of expression, is to over-express specific enzyme subtypes in target cells and analyze their effect on cellular phenotype (Housey, et al., 1988; Persons, et al., 1988., Krauss, et al., 1989; Megidish & Mazurek, 1989; Borner et al., 1991, 1992 a,b; Su, et al., 1991, 1992; Watanabe, et al., 1992; Mischak, et al., 1993).

Over-expression of the PKC $\beta_1$ gene in specific immortal cell lines, such as Rat 6, CREF and C3H10T1/2, can induce morphological, biological and biochemical changes often observed in oncogene transformed cells (Housey, et al., 1988; Krauss, et al., 1989, Su, et al., 1992). In addition, cells over-expressing PKC $\beta_1$ are more sensitive to transformation by Ha-ras (Hsiao, et al., 1989) and Ad5 Su, et al., 1991). In the present study. applicants have determined if the PKC $\beta_1$ gene could cooperate with Ad5 transforming genes in Ad5 transformed RE cells resulting in an induction of the progression phenotype. Such an interaction was observed and TPA further enhanced anchorage independence in PKC $\beta_1$ expressing Ad5-transformed RE cells. As was previously found with spontaneous and oncogene-mediated progression (Babiss, et al., 1985; Duigou, et al., 1989; 1991), a single 24 hour exposure to the demethylating agent 5-azacytidine (AZA) resulted in revertant clones which displayed a stable extinction of the transformation progression phenotype. In PKC $\beta_1$ expressing E11 cells, AZA treatment was associated with a decrease in PKC $\beta_1$ RNA transcriptional rates and steady state mRNA and a reduction in PKC enzymatic activity [$^3$H]-PDBu binding to cell surface phorbol ester receptors and anchorage independence. These observations indicate that the state of progression in Ad5-transformed RE cells, resulting spontaneously or by increased expression of Ha-ras or PKC $\beta_1$, is mediated by a cellular progression-suppressor-gene(s) whose expression may be regulated by DNA methylation (Babiss, et al., 1985; Reddy, et al., 1993)

SUMMARY OF THE INVENTION

This invention provides a method of identifying a progression suppressor gene which comprises: a) introducing DNA containing a progression gene into a population of transformed cells; b) treating the introduced transformed cells from step (a) so as to induce the expression of at least one progression suppressor gene and cause a subpopulation of the cells to revert to a characteristic phenotype; c) selecting cells which express the progression suppressor gene and exhibit the characteristic phenotype; d) isolating mRNA from the cells from step (c); e) comparing the mRNA so obtained with mRNA obtained from the uninduced transformed cells as to identify mRNA expressed only by the cells from step (c); and f) isolating the gene encoding such mRNA so as to thereby identify the progression suppressor gene.

This invention further provides a method of identifying a progression suppressor gene which suppresses expression of long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and cause a subpopulation of the cell to selectively suppress the expression of the long terminal repeat regulated protein kinase C $\beta_1$ gene; and c) selecting cells which express the progression suppressor gene; d) isolating mRNA from the cells from step (c); e) comparing the mRNA so obtained with mRNA obtained from the uninduced transformed cells so as to identify mRNA only expressed by the cells from step (c); and f) isolating the gene encoding such mRNa so as to thereby identify the progression suppressor gene.

This invention provides a method of selecting a molecule capable of inhibiting the function of a long terminal repeat of a retrovirus comprising: a) introducing DNA containing the long terminal repeat regulated protein kinase C $\beta_1$ gene into a population of transformed cells; b) selecting cells from step a) which expresses protein kinase C $\beta_1$ gene; c) treating the selected cells with an amount of the molecule effective to inhibit the function of the long terminal repeat; and c) determining the level of expression of the protein kinase C $\beta_1$ gene, the decrease in the level of expression indicating that the molecule is capable of inhibiting the function of the long terminal repeat.

This invention provides a method of selecting a molecule capable of activating the function of a long terminal repeat of a retrovirus comprising: a) introducing DNA containing the long terminal repeat regulated protein kinase C $\beta_1$ gene into a population of transformed cells; b) selecting cells which expresses the protein kinase C $\beta_1$ gene; c) contacting the selected cells from step b) with an amount of the molecule effective to activate the function of the long terminal repeat; c) determining the level of expression of the protein kinase C $\beta_1$ gene, the increase in the level of expression indicating that the molecule is capable of activating the function of the long terminal repeat.

This invention provides a method of identifying a gene which inhibits the function of the long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor genes and suppress expression of the long terminal repeat regulated protein kinase C $\beta_1$ gene; and c) isolating the gene which inhibits the function of the long terminal repeat.

This invention provides a method of identifying a protein factor capable of inhibiting the function of the long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and to suppress expression of the long terminal repeat regulated protein kinase C $\beta_1$ gene; c) isolating and lysing the nuclei from the cell from step (b) to produce an extract; d) contacting the extract with the long terminal repeat; and e) isolating the protein factor which binds with the terminal repeat, thereby isolating the factor capable of inhibiting the function of the long terminal repeat.

This invention provides a method of identifying a gene which activates the function of the long terminal repeat of a retrovirus comprising: a) introducing DNA containing a long terminal repeat regulated protein kinase C $\beta_1$ gene into a transformed cell; b) treating the cells of step (a) so as to induce the expression of at least one progression suppressor gene and suppress expression of the long terminal repeat regulated protein kinase C $\beta_1$ gene; c) treating the induced cell from step b) with an amount of protein kinase C activating compound or an inhibitor of serine or threonine specific protein phosphatase effective to activate the long terminal repeat; and d) isolating a gene which activates the long terminal repeat.

This invention provides a method of identifying a protein factor capable of activating the function of the long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and suppress expression of the long terminal repeat regulated protein kinase C $\beta_1$ gene; c) treating the induced cell from step b) with an amount of a protein kinase C activating compound or an inhibitor of serine or threonine specific protein phosphatase effective to activate the long terminal repeat; d) isolating and lysing the nuclei from the cell from step c to produce an extract; e) contacting the extract with DNA containing the long terminal repeat; and f) isolating the protein factor which binds with the terminal repeat, thereby identifying the factor capable of activating the function of the long terminal repeat.

DETAILED DESCRIPTION OF THE INVENTION

Figure 1:
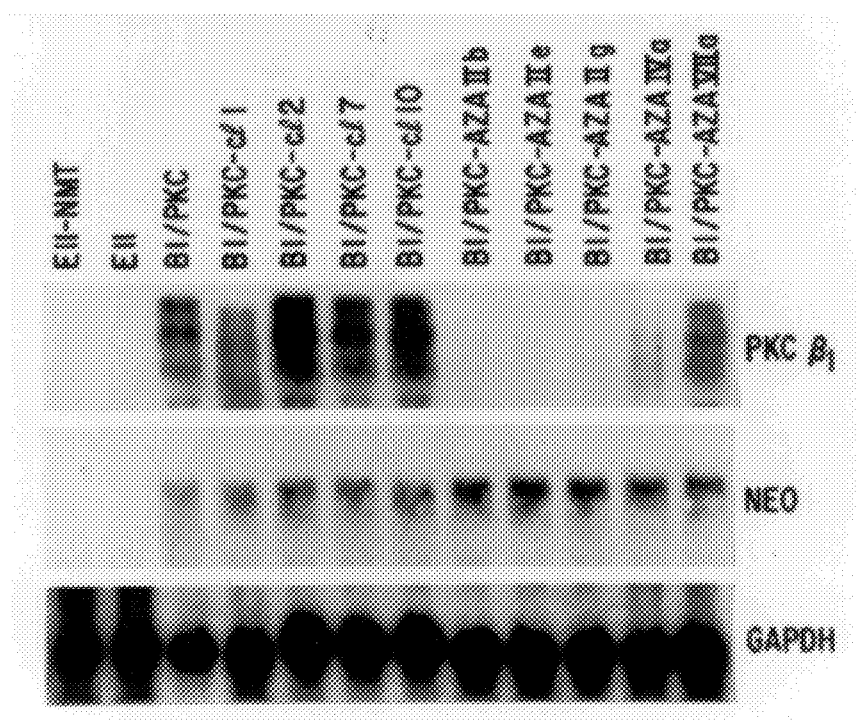
FIG. 1 Analysis of steady state levels of PKC $\beta_1$, neomycin resistance (NEO) and GAPDH mRNA expression in E11 and E11 subclones. Northern analysis using 15 µg of total cytoplasmic mRNA from logarithmically growing cells was performed as previously described (Babiss, et al., 1983; Su & Fisher, 1992). Cell lines include E11, E11-NMT (nude mouse tumor-derived E11 subclone), the PKC $\beta_1$ expressing E11 subclone B1/PKC, single-cell subclones of B1/PKC (B1/PKC-cl1, B1/PKC-cl2, B1/PKC-cl7 and B1/PKC-cl10) and single-cell subclones of B1/PKC cells treated for 24 hours prior to isolation with 10 µM AZA (B1/PKC-AZAIIb, B1/PKC-AZAIIe, B1/PKC-AZAIIg, B1/PKC/AZAIVa and B1/PKC-AZAVIIa).

Throughout this application, the following standard abbreviations are used to indicate specific nucleotides:

| | |
|---|---|
| C = cytosine | A = adenosine |
| T = thymidine | G = guanosine |

This invention provides a method of identifying a progression suppressor gene which comprises: a) introducing DNA containing a progression gene into a population of transformed cells; b) treating the introduced transformed cells from step (a) so as to induce the expression of at least one progression suppressor gene and cause a subpopulation of the cells to revert to a characteristic phenotype; c) selecting cells which express the progression suppressor gene and exhibit the characteristic phenotype; d) isolating mRNA from the cells from step (c); e) comparing the mRNA so obtained with mRNA obtained from the uninduced transformed cells as to identify mRNA expressed only by the cells from step (c); and f) isolating the gene encoding such mRNA so as to thereby identify the progression suppressor gene.

This invention provides a method of identifying a progression suppressor gene which suppresses the progression phenotype of a transformed cell comprising: a) introducing a progression gene into a transformed cell; b) selectively suppressing the progression phenotype by inducing expression of at least one progression suppressor gene; and c) isolating the progression suppressor gene.

The progression suppressor gene may be identified by subtractive hybridization or differential display. Subtractive hybridization techniques are well-known in the art. Differential display for differential expression cloning was also known (Sager et al. 1993; Liang & Pardee, 1992; Sun, et al., 1994).

The progression phenotype may be selectively suppressed by chemicals such as azacytidine or phenyl butyrate. Such treatment will induce expression of at least one progression suppressor gene and as a consequence, the progression phenotype is suppressed.

This invention provides the progression suppressor gene identified by the above described method. This identified gene would be useful in further study of regulation of the suppression and progression of the transformed phenotype. The progression suppressor gene could prove useful for diagnostic applications in tumor staging and for therapeutic uses.

The progression suppressor gene described and claimed herein are useful for the information which they provide concerning the amino acid sequence of the polypeptide and as products for the large scale synthesis of the polypeptide by a variety of recombinant techniques. The gene is useful for generating new cloning and expression vectors, transformed and transfected procaryotic and eucaryotic host cells, and new and useful methods for cultured growth of such host cells capable of expression of the polypeptide and related products.

This invention further provides the progression suppressor gene operatively linked to a promoter of RNA transcription.

This invention provides a vector which comprises the identifed progression suppressor gene. Suitable vectors comprise, but are not limited to, a plasmid or a virus. These vectors may be transformed into a suitable host cell to form a host cell vector system for the production of a polypeptide of the identified progression suppressor gene.

This invention provides a virus comprising the identified progression suppressor gene.

This invention provides a polypeptide encoded by the identified progression suppressor gene.

This invention further provides a method of identifying a progression suppressor gene which suppresses expression of long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and cause a subpopulation of the cell to selectively suppress the expression of the long terminal repeat regulated protein kinase C $\beta_1$ gene; and c) selecting cells which express the progression suppressor gene; d) isolating mRNA from the cells from step (c); e) comparing the mRNA so obtained with mRNA obtained from the uninduced transformed cells so as to identify mRNA only expressed by the cells from step (c); and f) isolating the gene encoding such mRNA so as to thereby identify the progression suppressor gene.

This invention provides a method of identifying a progression suppressor gene which suppresses expression of long terminal repeat of a retrovirus comprising: a) introducing a long terminal repeat regulated protein kinase C $\beta_1$ gene into a transformed cell; b) selectively suppressing expression of the long terminal repeat regulated protein kinase C $\beta_1$ gene by inducing the expression of at least one progression suppressor gene; and c) isolating the progression suppressor gene.

In an embodiment, the retrovirus is a Moloney leukemia virus long terminal repeat. In another embodiment, the retrovirus is a human immunodeficiency virus.

In one embodiment of this invention, the selective suppression of expression of the long terminal repeat regulated protein kinase C $\beta_1$ gene by inducing the expression of at least one progression suppressor gene was achieved by treatment with 5-azacytidine or phenyl butyrate. In another embodiment, the selective suppression is achieved by treatment with a DNA demethylating agent. DNA demethlating agents are well-known in the art.

This invention further provides that the progression suppressor gene may be isolated by subtractive hybridization or differential display.

This invention also provides the progression suppressor gene identified by the above-described method. This invention provides the progression suppression gene operatively linked to a promoter of RNA transcription. This invention provides a vector which comprises the identified progression suppressor gene. This invention also provides a virus comprising the identified progression suppressor gene. This invention further provides a polypeptide encoded by the identified progression suppressor gene.

This invention provides a method of selecting a molecule capable of inhibiting the function of a long terminal repeat of a retrovirus comprising: a) introducing DNA containing the long terminal repeat regulated protein kinase C $\beta_1$ gene into a population of transformed cells; b) selecting cells from step a) which expresses protein kinase C $\beta_1$ gene; c) treating the selected cells with an amount of the molecule effective to inhibit the function of the long terminal repeat; and c) determining the level of expression of the protein kinase C $\beta_1$ gene, the decrease in the level of expression indicating that the molecule is capable of inhibiting the function of the long terminal repeat.

This invention also provides a method of selecting a molecule capable of inhibiting the function of a long terminal repeat of a retrovirus comprising: a) introducing the long terminal repeat regulated protein kinase C $\beta_1$ gene into a transformed cell; b) contacting the cell from step a) with an amount of the molecule effective to inhibit the function of the long terminal repeat; and c) determining the level of expression of the protein kinase C $\beta_1$ gene, the decrease in the level of expression indicating that the molecule is capable of inhibiting the function of the long terminal repeat.

In an embodiment of the above method, the retrovirus is Moloney leukemia virus. In another embodiment, the retrovirus is human immunodeficiency virus.

This invention provides a method of selecting a molecule capable of activating the function of a long terminal repeat of a retrovirus comprising: a)introducing the long terminal repeat regulated protein kinase C $\beta_1$ gene into a transformed cell; b) contacting the cell from step a) with an amount of the molecule effective to activate the function of the long terminal repeat; c) determining the level of expression of the protein kinase C $\beta_1$ gene, the increase in the level of expression indicating that the molecule is capable of activating the function of the long terminal repeat.

This invention provides a method of identifying a gene which inhibits the function of the long terminal repeat of a retrovirus comprising: a)introducing a long terminal repeat regulated protein kinase C $\beta_1$ gene into a transformed cell; b) selectively suppressing expression of the long terminal repeat regulated protein kinase C $\beta_1$ gene in the introduced cell of step a) by inducing the expression of at least one progression suppressor gene; and c) isolating the gene which inhibits the function of the long terminal repeat. In an embodiment, the gene is isolated by subtractive hybridization or differential display.

This invention further provides the gene identified by the above-described method. This invention also provides the identified gene operatively linked to a promoter of RNA transcription. This invention further provides a vector which comprises the above gene. This invention provides a virus comprising the above gene. This invention also provides a polypeptide encoded by the above gene.

This invention provides a method of identifying a protein factor capable of inhibiting the function of the long terminal repeat of a retrovirus comprising: a) introducing a long terminal repeat regulated protein kinase C $\beta_1$ gene into a transformed cell; b) selectively suppressing expression of the long terminal repeat regulated protein kinase C $\beta_1$ gene in the introduced cell of step a) by inducing the expression of at least one progression suppressor gene; c) isolating and lysing the nuclei from the cell from step b to produce an extract; d) contacting the extract with the long terminal repeat; and e) isolating the protein factor which binds with the terminal repeat, thereby isolating the factor capable of inhibiting the function of the long terminal repeat. This invention provides the protein factor identified by the above-described method.

This invention provides a method of identifying a gene which activates the function of the long terminal repeat of a retrovirus comprising: a) introducing a long terminal repeat regulated protein kinase C $\beta_1$ gene into a transformed cell; b) selectively suppressing expression of the long terminal repeat regulated protein kinase C $\beta_1$ gene by inducing the expression of at least one progression suppressor gene; c) treating the induced cell from step b) with a protein kinase C activating compound or an inhibitor of serine or threonine specific protein phosphatase to activate the long terminal repeat; and d) isolating a gene which activates the long terminal repeat. In an embodiment, the gene is isolated by subtractive hybridization or differential display.

In an embodiment, the protein kinase C activating compound is a tumor promoting diterpene phorbol ester. In an another embodiment, the protein kinase C activating compound is a synthetic activator of protein kinase C. An example of this compound is ADMB and another example is DHI.

In another embodiment, an inhibitor of serine or threonine specific protein phosphatase is used to activate the protein kinase C $\beta_1$. An example of this serine or threonine specific protein phosphatase is calyculin. Another example is okadaic acid.

This invention further provides the gene identified by the above-described method. This invention also provides the identified gene operatively linked to a promoter of RNA transcription. This invention further provides a vector which comprises the above gene. This invention provides a virus comprising the above gene. This invention also provides a polypeptide encoded by the above gene.

This invention provides a method of selecting a molecule capable of activating the function of a long terminal repeat of a retrovirus comprising: a) introducing DNA containing the long terminal repeat regulated protein kinase C $\beta_1$ gene into a population of transformed cells; b) selecting cells which expresses the protein kinase C $\beta_1$ gene; c) contacting the selected cells from step b) with an amount of the molecule effective to activate the function of the long terminal repeat; c) determining the level of expression of the protein kinase C $\beta_1$ gene, the increase in the level of expression indicating that the molecule is capable of activating the function of the long terminal repeat.

This invention provides a method of identifying a gene which inhibits the function of the long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor genes and suppress expression of the long terminal repeat regulated protein kinase C $\beta_1$ gene; and c) isolating the gene which inhibits the function of the long terminal repeat.

This invention provides a method of identifying a protein factor capable of inhibiting the function of the long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and to suppress expression of the long terminal repeat regulated protein kinase C $\beta_1$ gene; c) isolating and lysing the nuclei from the cell from step (b) to produce an extract; d) contacting the extract with the long terminal repeat; and e) isolating the protein factor which binds with the terminal repeat, thereby isolating the factor capable of inhibiting the function of the long terminal repeat.

This invention provides a method of identifying a gene which activates the function of the long terminal repeat of a retrovirus comprising: a) introducing DNA containing a long terminal repeat regulated protein kinase C $\beta_1$ gene into a transformed cell; b) treating the cells of step (a) so as to induce the expression of at least one progression suppressor gene and suppress expression of the long terminal repeat regulated protein kinase C $\beta_1$ gene; c) treating the induced cell from step b) with an amount of protein kinase C activating compound or an inhibitor of serine or threonine specific protein phosphatase effective to activate the long terminal repeat; and d) isolating a gene which activates the long terminal repeat.

This invention provides a method of identifying a protein factor capable of activating the function of the long terminal repeat of a retrovirus comprising: a) introducing DNA containing a long terminal repeat regulated protein kinase C $\beta_1$ gene into a population of transformed cells; b) treating the cells from step (a) so as to induce the expression of at least one progression suppressor gene and suppress expression of the long terminal repeat regulated protein kinase C $\beta_1$ gene; c) treating the induced cell from step b) with an amount of a protein kinase C activating compound or an inhibitor of serine or threonine specific protein phosphatase effective to activate the long terminal repeat; d) isolating and lysing the nuclei from the cell from step c to produce an extract; e) contacting the extract with DNA containing the long terminal repeat; and f) isolating the protein factor which binds with the terminal repeat, thereby identifying the factor capable of activating the function of the long terminal repeat.

This invention also provides a method of identifying a protein factor capable of activating the function of the long terminal repeat of a retrovirus comprising: a) introducing a long terminal repeat regulated protein kinase C $\beta_1$ gene into a transformed cell; b) selectively suppressing expression of the long terminal repeat regulated protein kinase C $\beta_1$ gene in the introduced cell of step a) by inducing the expression of at least one progression suppressor gene; c) treating the induced cell from step b) with a protein kinase C activating compound or an inhibitor of serine or threonine specific protein phosphatase to activate the long terminal repeat; d) isolating and lysing the nuclei from the cell from step c) to produce an extract; e) contacting the extract with the long terminal repeat; and f) isolating the protein factor which binds with the terminal repeat, thereby identifying the factor capable of activating the function of the long terminal repeat. Finally this invention provides the identifed protein factor described by the above method.

This invention provides a powerful tool for identifying critical transcriptional regulators, both activators and inhibitors, controlling expression of LTRs of retroviruses. Once appropriate DNA-binding proteins are identified, they can serve as models for designing drugs which can be used to specifically inhibit replication of viruses controlled by LTRs, i.e., such as HIV which is the mediator of AIDS. In addition, replicating retroviruses containing dominant acting genes which encode proteins functioning as transcriptional suppressors of LTRs could be transferred into uninfected T-cells preventing subsequent production of HIV after infection. Another approach could be to use the genes encoding mutated activators of LTR expression as dominant-negative mutants to infect uninfected T-cells preventing subsequent production of HIV following infection. The approaches briefly outlined above represent novel strategies for: designing new classes of compounds to inhibit HIV replication; constructing viruses (which can function as potential vaccines) preventing HIV-infected T-cells from producing new viruses; and generating retroviruses which can prevent uninfected T-cells from producing new progeny HIV and releasing virus capable of infecting additional target T-cells. These approaches used alone or in various combinations could result in the effective treatment of HIV-infected individuals and a means of curtailing HIV pathogenesis.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

MATERIALS AND METHODS

Cell cultures

E11 is a single-cell clone of H5ts125-transformed Sprague-Dawley secondary RE cells (Fisher et al., 1978). E11-NMT is a subclone of cells derived from a nude mouse tumor (Babiss et al., 1985). E11/pNV7-J3 and E11/pMV7-K2 are two independent neomycin (neo) resistant E11 cultures obtained following transfection with pMV7 (Perkins, et al., 1983) and selection for growth in G418. A1/PKC, B1/PKC, C1/PKC and D1/PKC are four independent neo resistant E11 cultures obtained following transfection with a full-length cDNA sequence of RP58 (Housey, et al., 1987), which encodes $PKC\beta_1$, subcloned into pMV7 (pMV7-PKC) (Housey, et al., 1988) and selection for G418 resistance. B1/PKC subclones, B1/PKC-cl1, B1/PKC-cl2, B1/PKC-cl7 and B1/PKC-cl10, were obtained by plating B1/PKC cells at low density and isolating independent single-cell derived clones using a metal cloning cylinder (Fisher, et al., 1978). AZA treated subclones of E11, E11-NMT, A1/PKC, B1/PKC, C1/PKC and D1/PKC were obtained by plating cells at low density, adding 10 $\mu$m AZA for 24 hours, removing AZA and growing cells in AZA-free culture medium for three weeks and isolating single-cell derived clones (Babiss, et al., 1985). All cultures were grown in Dulbecco's modified Eagle's medium supplemented with 5% FBS (DMEM-5) at 37° C. in a humidified 5% $CO_2$/95% air incubator.

A B1/PKC adenovirus type 5 (H5ts125) transformed Sprague-Dowley rat embryo clone (E11) was deposited on Mar. 30, 1998 with the American Type Culture Collection (ATCC), 10801 University Blvd., Manassas, Va. 20110-2209, U.S.A. under the provisions of the Budapest Treaty for the International Recognition of the Deposit of Microorganism for the Purposes of Patent Procedure. This deposit was accorded ATCC Accession Number CRL-12499.

DNA transfections

E11 cells were seeded at $1\times10^5$ cells per 10 cm plate; 24 hours later cultures were transfected using the calcium phosphate precipitation method with 10 $\mu$g of pMV7 or pMV7-PKC as described previously with slight modifications (Babiss, et al., 1984; Su, et al., 1990). Approximately 48 hours after transfection, cultures were seeded at $1\times10^5$ and $5\times10^5$ per 6 cm plate in G418 (1000 $\mu$g ml$^{-1}$) containing medium and the medium with G418 was changed every three or four days until neo resistant colonies developed (approximately two weeks). G418-resistant E11 subclones were isolated and maintained as separate clonal populations in media containing 250 $\mu$g ml$^{-1}$ G418.

Anchorage-independent growth

The ability of the various cell lines to grow when suspended in soft agar was determined as described previously (Fisher, et al., 1979c). Cells were initially seeded in agar at different cell densities ranging from a high of $5\times10^4$ to a low of $2\times10^3$. After 21 days of growth in DMEM containing 7.5% FBS and 0.4% noble agar with routine feeding every four days, colonies >0.1 mm in diameter were counted with the aid of an Olympus tissue culture microscope and a calibrated grid. For cultures receiving TPA, 100 ng ml$^{-1}$ of TPA was incorporated in the 0.8% noble agar/DMEM-7.5 base layer, the 0.4% noble agar/DMEM-7.5 overlay layer and the 0.4% noble agar/DMEM-7.5 overlay feeder layers.

PKC-enzymatic activity

Levels of PKC enzymatic activity were determined using DEAE-fractionated cell lysates (O'Brian, et al., 1989). Lysates were prepared by harvesting cells in the logarithmic phase of growth with Buffer A (20 mM Tris-HCl pH 7.5, 5 mM EDTA, 5 mM EGTA, 15 mM 2-mercaptoethanol, 10 $\mu$g ml$^{-1}$ leupeptin, 0.25 mM PMSF, 25 $\mu$g ml$^{-1}$ soybean trypsin inhibitor) containing 0.1% Triton X-100, stirring the cell suspensions for 1 hour, and then centrifuging them at 13,800 G for 15 min. Supernatants were loaded onto 0.5 ml DEAE-Sepharose columns equilibrated in Buffer A. Columns were washed with 3 ml of Buffer A, and 2 ml of Buffer A containing 0.2M NaCl (pH 7.5) was used to elute PKC activity (O'Brian et al., 1989). PKC enzymatic activity was assayed as previously described (Ward & O'Brian, 1992), by subtracting the phosphotransferase activity between [$\gamma^{32}$P] ATP and histone III-S observed in the presence of 1 mM $Ca^{2+}$ from the activity observed in the presence of 1 mm $Ca^{2+}$ plus 30 $\mu$g PS/ml.

Cellular ($^3$H)-PDBu binding

PDBu binding assays were performed as described by Housey et al. (1988) and Su et al. (1992). Cells were seeded at $2\times10^3$/35 mm tissue culture plate, DMEM-5 was added 24 hour post-plating and cells were assayed 20 to 24 hours later. Cultures were washed 2×with DMEM:PBS:BSA (2:1 vol/vol, DMEM:PBS, containing 1.0 mg ml$^{-1}$ bovine serum fraction V (Sigma) and incubated at 37° C. in the presence of 1.0 ml of DMEM:PBS:BSA containing 50 or 25 nM [$^3$H]-PDBu (New England Nuclear; 8.3 Ci mmol$^{-1}$). Four replicate plates were incubated with [$^3$H]-PDBu while a fifth plate was incubated with [$^3$H]-PDBu in the presence of 50 nM unlabeled PDBu to determine nonspecific binding. Two additional plates were re-suspended by brief trypsin/versene treatment and counted using a model $Z_m$ Coulter Counter (Hialeah, Fla.). Plates receiving PDBu were washed 3×in 3 ml of ice-cold DMEM:PBS:BSA and solubilized for 2 hours at 37° C. using 1.2 ml of 2.25% trypsin, 0.02% EDTA, 1.0% Triton X-100. One ml of lysate was counted by liquid scintillation.

Nucleic acid analysis

High molecular weight DNA was isolated from the various cells as previously described (Dorsch-Hasler, et al., 1908; Fisher, et al., 1982; Babiss, et al., 1984). Cellular DNAs (10 $\mu$g per sample) were digested with the restriction endonuclease EcoRI, size-fractionated through 0.6% agarose gels, transferred to nitrocellulose filters and probed using a $^{32}$P-labeled PKC $\beta_1$ DNA probe as described previously (Fisher, et al., 1982). Steady state levels of PKC $\beta_1$ Ad5 E1A, neo, Ad5 E1B, c-jun, PKCε and GAPDH mRNAs were determined by Northern analysis of total cytoplasmic RNA using appropriate multiprimed $^{32}$P-labeled cloned DNA probes as described previously (Babiss, et al., 1983; Su & Fisher, 1992). Northern blots were washed in a 0.1% SDS, 1×SSC buffer at room temperature for 30 min followed by washing at 42° C. for an additional 30 min in the same buffer. In vitro transcription within isolated nuclei was performed as previously described (Friedman, et al., 1986; Duigou, et al., 1990; Su, et al., 1993) with modifications (Jiang, et al., 1993). Nuclei from approximately 2×10$^6$ cells were isolated, and RNA transcripts previously initiated by RNA polymerase II were allowed to elongate in the presence of [$^{32}$P]UTP. The [$^{32}$P]-labeled RNA was extracted with phenol/chloroform and unincorporated nucleotides were removed by passing the probe through a G-50 Sephadex column. Nylon membranes containing 2 μg of the appropriate denatured plasmid DNA gene inserts were hybridized with the [$^{32}$P]-labeled RNA. Nylon membranes contained PKCα, PKC $\beta_1$, PKCγ, PKCε, c-jun, jun-B, c-fos, Ad5 E1A, Ad5 E1B, GAPDH, β-actin and pBR322 DNA probes. Following hybridization, the nylon membranes were washed and exposed for autoradiography.

Gel-retardation assays

Oligonucleotide probes were synthesized which contain the AP-1 binding sequence (5'CCAAACAGGATATATGAGTCATGCAGTTC-3') (SEQ. ID NO: 1) (Angel, et al., 1988; Mitchell & Tijian, 1989) or the MECA binding sequence (5'-CCAAACAGGATATCTGTGGTAAGCAGTTCC-3') (SEQ. ID NO: 2) (Halazonetis, 1992). Oligonucleotides were end-labeled with [$^{32}$P-γ]-ATP using T$_4$ DNA kinase and then allowed to react with nuclear extracts at room temperature for 30 min. Reaction mixtures consisted of $^{32}$P-labeled oligonucleotide (5000 c.p.m.), 2 μg of poly (dI-dC) and 10 μg of nuclear protein extract in 10 mM HEPES (pH 7.5), 50 mM KCl, 5 mM MgCl$_2$, 0.5 mM EDTA, 1 mM DTT and 12.5% glycerol. After incubation for 30 min at room temperature the reaction mixtures were separated on a 5% polyacrylamide gel with circulating Tris-borate buffer (0.375×TBE, 160V), the gels were dried and autoradiographed. Nuclear extracts were also incubated with a 100-fold excess of unlabeled competitor DNA and the $^{32}$P-labeled oligonucleotide probes.

EXPERIMENTAL RESULTS

Induction of the transformation progression phenotype by the PKC $\beta_1$ gene in Ad5-transformed RE cells In Ad5-transformed Sprague-Dawley RE cells, the ability to form colonies in agar with enhanced efficiency correlates directly with increased tumorigenic potential in nude mice, i.e., the progression phenotype (Fisher, et al., 1979a, b, c; Babiss, et al., 1985; Duigou, et al., 1989, 1991). The Ad5-transformed RE clone, E11, grows with a lower efficiency in agar and displays a longer latency time for tumor formation in nude mice than its progressed nude mouse tumor-derived subclone, E11-NMT (Babiss, et al., 1985) (Table 1 and data not shown). Transfection of E11 cells with a cloned PKC $\beta_1$ gene construct which also contains a neomycin (neo) resistance gene (Housey, et al., 1988) results in G-418 resistant clones that display enhanced anchorage independence in comparison with parental E11 cells (Table 1). In contrast, G418-resistant E11 cells transfected with the pMV7 plasmid construct lacking the PKC $\beta_1$ expressing E11 clones also display a reduction in tumor latency time in nude mice (data not shown). As observed previously with E11 and E11-NMT cells, TPA increased the efficiency of agar growth in PKC $\beta_1$ transfected E11 cells (Table 1). These results indicate that the PKC $\beta_1$ gene can function as a progression-inducing gene in E11 cells and this process can be further modulated by the phorbol ester tumor promoter, TPA.

TABLE 1

Effect of TPA on anchorage-independent growth of Ad5-transformed rat embryo cells (E11), nude mouse tumor-derived E11 cells (E11-NMT), G418-resistant pMV7transformed E11 cells and E11 cells expressing the $\beta_1$ isoform of PKC

| Cell type[a] | Cloning efficiency in agar (%)[b] | | Phenotype[c] |
|---|---|---|---|
| | −TPA | +TPA | |
| E11 | 4.2 ± 0.8 | 6.1 ± 0.6 (1.5) | P− |
| E11-NMT | 32.7 ± 2.9 | 53.4 ± 4.5 (1.6) | P+ |
| E11/pMV7-J3 | 2.8 ± 0.4 | 3.5 ± 0.4 (1.3) | P− |
| E11/pMV7-K2 | 4.4 ± 0.7 | 5.9 ± 0.3 (1.3) | P− |
| A1/PKC | 12.4 ± 1.1 | 20.1 ± 0.9 (1.6) | P+ |
| B1/PKC | 29.1 ± 1.3 | 56.8 ± 3.5 (2.0) | P+ |
| C1/PKC | 10.1 ± 0.7 | 17.1 ± 1.2 (1.7) | P+ |
| D1/PKC | 22.6 ± 2.2 | 49.5 ± 2.8 (2.2) | P+ |

[a]Cell lines include the parental E11 cell line, a nude mouse tumor-derived E11 clone (E11-NMT). G418-resistant E11 cells obtained following transfection with the pMV7 vector (E11/pMV7-J3 and E11/pMV7-K2), and PKC $\beta_1$ expressing E11 clones (A1/PKC, B1/PKC). C1/PKC and D1/PKC.
[b]Agar cloning effeciency, in the absence or presence of 100 ng ml$^{-1}$ of TPA, was determined as described in Materials and Methods and previousiy (Fisher, et al., 1979c). Results presented are the average percent agar cloning efficiency ± SD of 4 replicate plates initially seeded with 5 × 10$^4$ cells. Values presented in brackets refer to fold-increase in agar cloning in the presence of TPA
[c]Progression phenotype (P+) and absence of the progression phenotype (P−). Progression phenotype is indicated by enhanced growth in agar in comparison with parental E11 cells with a further increase in anchorage-independent growth after exposure to TPA.

Reversal of the transformation progression phenotype in E11-PKC $\beta_1$ cells by AZA The progression phenotype of E11-NMT cells can be stably reversed by a single-application of the demethylating agent AZA (Babiss, et al., 1985). Growth of E11-NMT and PKC $\beta_1$-transfected E11 cells at clonal cell densities (100 and 200 cells/6 cm plate) for 24 hours in the presence of 10 μM AZA, followed by continued cultivation for two weeks in the absence of AZA resulted in a series of AZA subclones displaying a stable reversion in their anchorage-independence to that of parental E11 cells (Table 2). In contrast, AZA-treatment did not modify the low anchorage-independence of E11 cells or of neo resistant E11 cells transformed with the pMV7 construct lacking the PKC $\beta_1$ gene (Table 2 and data not shown). These observations indicate that AZA can also reverse the progression phenotype in PKC $\beta_1$ expressing E11 cells as observed previously in spontaneously progressed and Ha-ras-progressed E11 cells treated with AZA (Babiss, et al., 1985; Duigou, et al., 1989).

TABLE 2

Effect of AZA on anchorage-independent growth of E11 and E11 subclones

| Cell type[a] | AZA treatment[†] | Cloning efficiency in agar (%)↓ | Phenotype[+] |
|---|---|---|---|
| E11 | − | 3.5 ± 0.5 | P− |
| E11-AZA 1 | + | 4.6 ± 0.4 | P− |
| E11-AZA 2 | + | 6.1 ± 0.5 | P− |
| E11-NMT | − | 35.3 ± 2.6 | P+ |
| E11-NMT-AZA 1 | + | 4.3 ± 0.6 | P− |
| E11-NMT-AZA 2 | + | 2.7 ± 0.3 | P− |
| A1/PKC | − | 11.8 ± 0.9 | P+ |
| A1/PKC-AZAIa | + | 1.6 ± 0.2 | P− |
| A1/PKC-AZAIIi | + | 4.1 ± 0.4 | P− |
| B1/PKC | − | 27.5 ± 1.8 | P+ |
| BP/PKC-AZAIIg | + | 4.3 ± 0.5 | P− |
| B1/PKC-AZAIVe | + | 1.8 ± 0.1 | P− |
| C1/PKC | − | 12.2 ± 1.0 | P+ |
| C1/PKC-AZAIIId | + | 4.9 ± 0.4 | P− |
| C1/PKC-AZAVa | + | 7.1 ± 0.8 | P− |
| D1/PKC | − | 24.8 ± 1.7 | P+ |
| D1/PKC-AZAVIb | + | 8.1 ± 1.0 | P− |
| D1/PKC-AZAVIIc | + | 4.3 ± 0.6 | P− |

[a]Cell lines have been described in the legend to Table 1 and in Materials and Methods. [†]The indicated cell type was treated at clonal densities with 10 μM AZA for 24 h., cultures were grown for two weeks in the absence of AZA and independent colonies were isolated and maintained as separate clones (termed AZA clones). AZA treatment = +; no AZA treatment = −. ↓ Results presented are the average percent agar cloning efficiency ± SD of four replicate plates initially seeded with 5 × 10⁴ cells. Further details in Materials and Methods. [+]Progression phenotype (P+) and absence of the progression phenotype (P−). Progression phenotype is indicated by enhanced growth in agar in comparison with parental E11 cells.

Molecular and biochemical properties of B1/PKC cells and AZA-revertant B1/PKC cells To investigate the mechanism by which the PKC $\beta_1$ gene induces the progression state and AZA reverts progression in PKC $\beta_1$ expressing cells applicants utilized the PKC $\beta_1$/neo-construct transfected G418-resistant E11 subclone, B1/PKC (Tables 1 and 2). Southern hybridization analysis of EcoRI digested DNA isolated from B1/PKC cells and its single-cell derived-untreated-subclones, B1/PKC-cl1, B1/PKC-cl2, B1/PKC-cl7 and B1/PKC-cl10, and its single-cell derived-AZA-treated subclones, B1/PKC-AZAIIb, B1/PKC-AZAIIe, B1/PKC-AZAIIg, B1/PKC-AZAIVa and B1/PKC-AZAVIIa, indicated the presence of a 2.4 kb fragment corresponding to the newly inserted PKC $\beta_1$ gene (data not shown). This DNA fragment was not present in E11 or E11-NMT cells, whereas additional DNA fragments of approximately 11, 6.8, 4.1 3.1 and 1.5 kb that correspond to the endogenous PKC $\beta_1$ gene were present in all of the E11-derived cell lines (data not shown).

Figure 2:
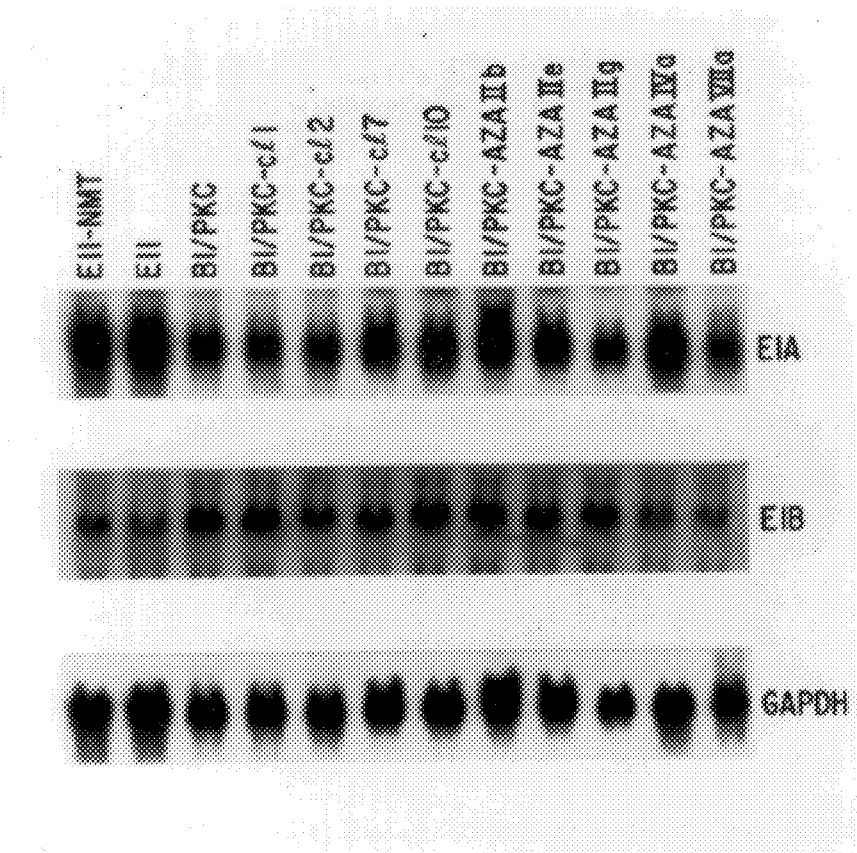
FIG. 2 Analysis of steady state levels of Ad5, E1A, Ad5 E1B and GAPDH mRNA expression in E11 and E11 subclones. Northern analysis using 15 µg of total cytoplasmic mRNA from logarithmically growing cells was performed as previously described (Babiss, et al., 1983; Su & Fisher, 1992). Cell line description can be found in the legend to FIG. 1.

As anticipated based on their ability to grow in G418, all of the B1/PKC and B1/PKC-AZA subclones expressed the neo resistance gene, whereas this mRNA was not detected in E11 or E11-NMT cells (FIG. 1). In addition, all of the B1/PKC-AZA subclones produced more neo resistance RNA then parental B1/PKC and many of the untreated B1/PKC subclones. Probing of Northern blots with a PKC $\beta_1$ gene demonstrated the presence of multiple hybridizing mRNAs from B1/PKC and its untreated subclones, whereas the majority of AZA-treated B1/PKC subclones contained reduced levels of these mRNAs (FIG. 1). The multiple hybridizing RNAs seen in B1/PKC cells and its subclones presumably represent unspliced transcripts or variably spliced transcripts coming from the retroviral promoter in the PKC $\beta_1$ vector pMV7-PKC$\beta_1$. The major transcript is a 6.6 kb RNA species, which corresponds to the predicted size for an mRNA transcript that initiates in the 5' LTR and terminates in the 3' LTR of pMV7-PKC$\beta_1$ construct. In contrast, probing similar Northern blots with the Ad5-E1A and E1B transforming genes indicated no consistent differences in expression of these genes in the various cell types (FIG. 2). These observations indicate that treatment with AZA results in: (a) a selective suppression in expression of the transfected PKC $\beta_1$ gene, without a similar suppression in expression of the neo resistance gene that is present on the same transfected plasmid construct; and (b) no change in expression of the Ad5 E1A or E1B genes as a function of expression or AZA-induced suppression of the transformation progression phenotype.

The biological and biochemical properties of B1/PKC cells and its untreated and AZA-treated subclones are shown in Table 3. Parental B1/PKC cells grew with increased efficiency in agar vs. E11 parental cells (Table 1). An increase in agar cloning efficiency was also apparent in all of the B1/PKC-derived untreated subclones (Table 3). E11, E11-NMT, B1/PKC and untreated B1/PKC subclones displayed a further enhancement in anchorage-independence of 1.4 to 2.3-fold when grown in the continuous presence of TPA (Table 3). B1/PKC and B1/PKC untreated subclones displayed increased levels of [³H]-PDBu binding to cell surface receptors in comparison with E11 and E11-NMT cells (Table 3). In parental B1/PKC cells and specific untreated B1/PKC subclones, the increase in binding of phorbol esters to cell surface receptors correlates with an increase in PKC enzymatic activity (Table 3). This was not always the case, however, as indicated by B1/PKC-cl10 cells that displayed elevated [³H]-PDBu binding to cell surface receptors without a significant increase in PKC enzymatic activity. Compared with the dramatic changes observed in phorbol ester binding levels, alterations in PKC enzymatic activity levels were relatively modest. This most likely reflects efficiencies of active enzyme recovery from cell lysates (phorbol ester binding assays are done in intact cells) and/or incomplete post-translational modification of PKC, resulting in a catalytically inactive form of the enzyme (Borner, et al., 1988).

TABLE 3

Growth in agar, binding of phorbol-dibutyrate (PDBu) and protein kinase C (PKC) activity in E11 cells and E11 cells expressing the $\beta_1$ isoform of PKC

| | Growth in Agar | | |
|---|---|---|---|
| | (%)[a] | | PDBu binding |
| Cell line | −TPA | +TPA | (c.p.m./10⁴ cells) |
| E11 | 2.5 | 3.5 (1.4) | 707 |
| E11-NMT | 39.9 | 58.4 (1.5) | 771 |
| B1/PKC | 28.7 | 57.9 (2.0) | 13,363 |
| B1/PKC-cl1 | 28.9 | 46.1 (1.6) | 13,758 |
| B1/PKC-cl2 | 16.6 | 38.2 (2.3) | 14,658 |
| B1/PKC-cl7 | 10.9 | 19.9 (1.8) | 16,211 |
| B1/PKC-cl10 | 20.3 | 38.6 (1.9) | 13,989 |
| B1/PKC-AZAIIb | 7.6 | 7.2 (0.9) | 651 |
| B1/PKC-AZAIIe | 6.1 | 7.4 (1.2) | 696 |
| B1/PKC-AZAIIg | 5.2 | 4.7 (0.9) | 1,133 |
| B1/PKC-AZAVIIa | 26.6 | 40.7 (1.5) | 39,942 |

| Cell line | PKC activity (mmol/min/mg)+ | Phenotype++ |
|---|---|---|
| E11 | N.D. | P− |
| E11-NMT | N.D. | P+ |
| B1/PKC | 1.83 ± 0.46 | P+ |
| B1/PKC-cl1 | 1.07 ± 0.34 | P+ |
| B1/PKC-cl2 | 1.61 ± 0.13 | P+ |
| B1/PKC-cl7 | 2.33 ± 0.27 | P+ |

TABLE 3-continued

Growth in agar, binding of phorbol-dibutyrate (PDBu) and protein kinase C (PKC) activity in E11 cells and E11 cells expressing the $\beta_1$ isoform of PKC

| | | |
|---|---|---|
| B1/PKC-cl10 | 0.37 ± 0.10 | P+ |
| B1/PKC-AZAIIb | 1.04 ± 0.54 | P− |
| B1/PKC-AZAIIe | 1.62 ± 1.14 | P− |
| B1/PKC-AZAIIg | 0.48 ± 0.53 | P− |
| B1/PKC/AZAVIIa | 3.36 ± 1.26 | P+ |

[a]E11, E11-NMT, PKC $\beta_1$ expressing E11 (B1/PKC), single-cell derived B1/PKC subclones (B1/PKC-cl1, B1/PKC-cl2, B1/KC-cl7 and B1/PKC-cl10 and single-cell derived B1/PKC subclones treated with 10 μM AZA for 24 h (B1/PKC-AZAIIb, B1/PKC-AZAIIe, B1/PKC-AZAIIg, and B1/PKC-AZAVIIa) were analyzed for anchorage-independent growth in the presence and absence of 100 ng ml$^{-1}$ of TPA as described previously (Fisher et al., 1979c). Results presented are the average percent agar cloning efficiency of 4 replicate plates. Replicate samples varied by <10%. Values presented in brackets refer to fold-increase in agar cloning in the presence of TPA.
PDBu binding assays were performed as described in Materials and Methods. Results presented are the average specific binding (corrected for non-specific binding) of four replicate plates. Replicate samples varied by <15%.
+PKC enzymatic activity was determined as described in Materials and methods. Results are the average of triplicate samples ± standard deviation of the mean.
++Progression phenotype (P+) and absence of the progression phenotype (P−). Progression phenotype is indicated by enhanced growth in agar in comparison with parental E11 cells with a further increase in anchorage-independent growth after exposure to TPA.

With the exception of B1/PKC-AZAVIIa, all of the AZA-treated B1/PKC subclones exhibited a reduction in anchorage-independence in comparison with parental B1/PKC cells. Similarly, except for B1/PKC-AZAVIIa cells, which behaved in a similar manner as E11, E11-NMT, B1/PKC and B1/PKC subclones not treated with AZA, TPA did not result in an increase in anchorage-independence in B1/PKC-AZA cells (Table 3). All of the B1/PKC-AZA clones, with the exception of B1/PKC-AZAVIIa, also displayed a reduction in [$^3$H]-PDBu binding to cell surface receptors and PKC enzymatic activity (Table 3). It should be noted that B1/PKC-AZAVIIa cells retained similar properties as B1/PKC cells, including the retention of $\beta_1$ PKC mRNA expression suggesting that this clone had not been reverted in its transformation progression phenotype by AZA (Table 3 and FIG. 1). These results indicate that increased expression of PKC $\beta_1$ in E11 cells is often associated with increased PKC enzymatic activity and enhanced binding of phorbol dibutyrate to PKC-cell surface receptors. In addition, whereas TPA can increase anchorage-independence in E11, E11-NMT and B1/PKC cells, it cannot induce this effect in B1/AZA clones displaying a loss of the progression phenotype.

Effect of TPA on gene expression in AZA-reverted B1/PKC cells

Figure 3:
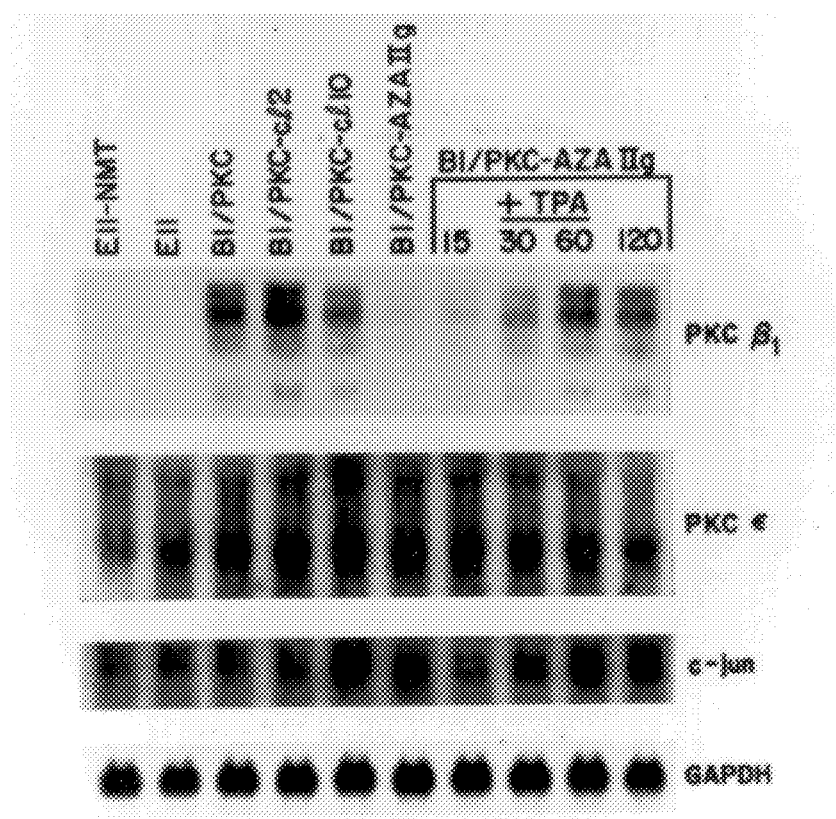
FIG. 3 Effect of TPA on expression of PKC $\beta_1$, PKCε, c-jun and GAPDH in B1/PKC-AZAIIg cells. Cells were treated with 100 ng ml$^{-1}$ of TPA for 15, 30, 60 or 120 minutes prior to RNA isolation and analysis by Northern hybridization. For comparison, mRNA samples from untreated E11-NMT, E11, B1/PKC, B1/PKC-cl1, B1/PKC-cl10 and B1/PKC-AZAIIg were analyzed.
Figure 4:
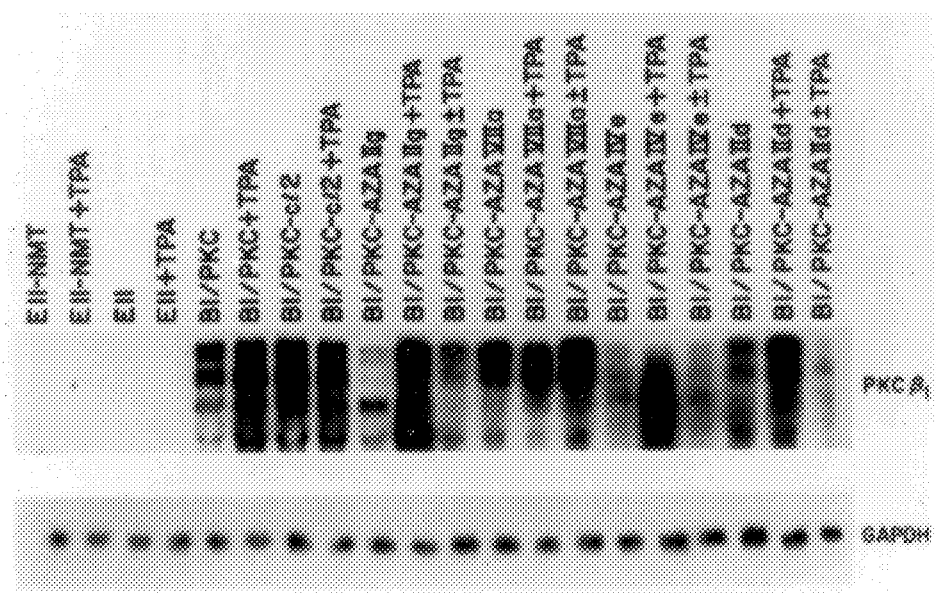
FIG. 4 Effect of continuous and transient TPA treatment on expression of PKC $\beta_1$ and GAPDH mRNA in E11 and E11 subclones. RNAs were isolated from untreated E11 and E11 subclones or subclones grown for 24 hours in the presence of 100 ng/ml$^{-1}$ of TPA (+TPA), or subclones grown for 24 hours in the presence of 100 ng ml$^{-1}$ of TPA followed by growth for one week in the absence of TPA (±TPA).

TPA is a potent activator of PKC in diverse target cells (reviewed in Ohno, et al., 1991; Nishizuka, 1992). To determine if TPA could alter gene expression in B1/PKC-AZAIIg cells, cultures were incubated with 50 ng ml$^{-1}$ of TPA for 15, 30, 60 and 120 minutes (FIG. 3). TPA resulted in a time-dependent induction of PKC $\beta_1$ expression in B1/PKC-AZAIIg cells that was first apparent by 30 minutes and maximum by 60 minutes. TPA also increased c-jun mRNA levels in B1/PKC-AZAIIg cells with similar kinetics as PKC $\beta_1$ induction. In contrast, TPA did not alter expression of the endogenous PKCε gene or the GAPDH gene in B1/PKC-AZAIIg cells (FIG. 3). TPA also did not significantly alter PKC $\beta_1$ mRNA levels in B1/PKC cells already displaying high levels of PKC $\beta_1$ mRNA, i.e., B1/PKC-cl2 and B1/PKC-AZAVIIa cells (FIG. 4). In B1/PKC-AZAIId cells, which display a higher level of de novo expression of PKC $\beta_1$ mRNA than B1/PKC-AZAIIg cells, TPA further enhanced PKC $\beta_1$ expression (FIG. 4). Preliminary studies indicate that additional agents can induce PKC $\beta_1$ mRNA expression in B1/PKC-AZAIIg cells, including calyculin and okadaic acid (inhibitors of serine/threonine-specific protein phosphatase 1 and 2A and 2B at higher concentrations) and rationally designed protein kinase C activators ADMB (3-(N-acetylamino)-5-(N-decyl-N-decyl-N-methylamino) benzyl alcohol) and DHI (6-(N-decylamino)-4-hydroxymethylindole) (unpublished data). To determine if the effect of TPA on $\beta_1$ PKC expression in B1/PKC-AZA treated subclones was reversible or irreversible, cells were grown for 24 hours in TPA, cultures were washed and incubated for an additional 7 days in the absence of TPA (FIG. 4). A reduction in PKC $\beta_1$ mRNA level was observed in B1/PKC-AZAIIg, B1/PKC-AZAIVe and B1/PKC-AZAIId cells grown for one week in the absence of TPA. This experiment indicates that the TPA effect on PKC $\beta_1$ expression depends on the level of PKC $\beta_1$ initially expressed by the B1/PKC subclones and the TPA effect is reversible following removal of this tumor promoting agent.

Figure 5:
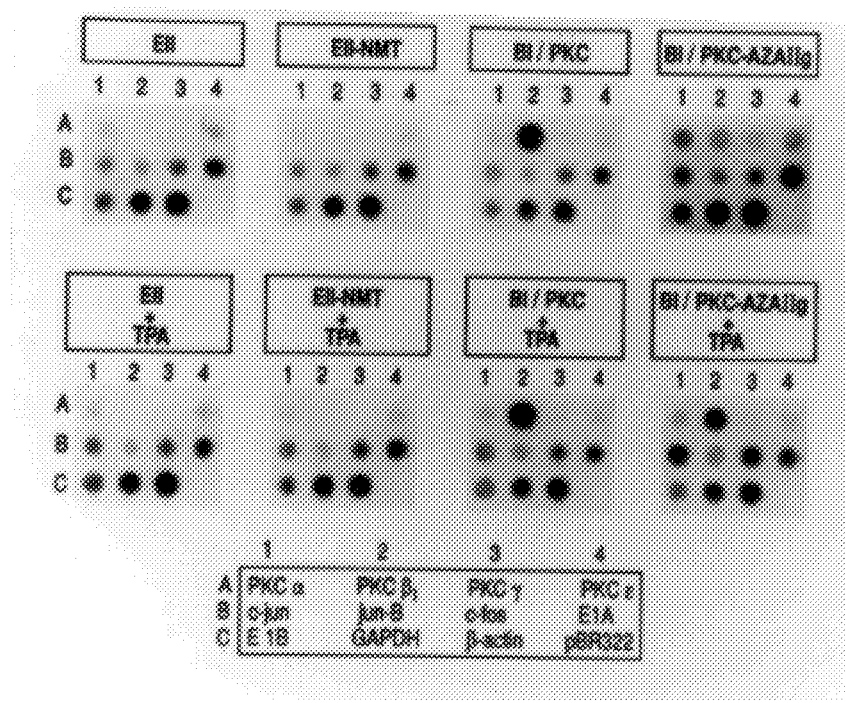
FIG. 5 Analysis of gene transcription rates in E11, E11-NMT, B1/PKC and B1/PKC-AZAIIg cells grown in the absence or presence of TPA. Nuclei from 2×10$^6$ cells were isolated from each cell line shown (either untreated or treated with 100 ng ml$^{-1}$ of TPA for one hour) and nuclear RNA was labeled in vitro and subsequently hybridized to denatured DNA probes on nylon membranes. For each hybridization reaction, an equal number of total counts representing a similar number of cell nuclei was used, so that the comparative rates of transcription could be obtained. The gene probes used are shown in the order presented in the box.

The ability of TPA to induce a rapid induction of PKC $\beta_1$ RNA in B1/PKC-AZAIIg cells suggested that TPA might be transcriptionally activating this gene. To investigate this possibility, applicants used nuclear run-on assays to measure RNA transcription rates in untreated and TPA-treated B1/PKC-AZAIIg cells (FIG. 5). As appropriate control cell lines, RNA transcription rates in the presence and absence of 1 hour treatment with 50 ng ml$^{-1}$ TPA were also determined in E11, E11-NMT and B1/PKC cells. Using GAPDH and β-actin as internal control indicators of RNA transcription, the transcription rates of the PKC α, PKC γ, PKC ε, Jun-B, Ad5 E1A and Ad5 E1B genes were similar (within two-fold) in all four cell types grown in the presence or absence of TPA (FIG. 5). Transcription of the PKC γ gene in all four cell types and the PKC $\beta_1$ gene in E11 and E11-NMT was negligible in the presence or absence of TPA. In contrast, the inserted PKC $\beta_1$ gene was transcribed at a high rate in B1/PKC cells, whereas transcription of this gene was reduced >10-fold in B1/PKC-AZAIIg cells (FIG. 5). When treated with 50 ng ml$^{-1}$ of TPA for 1 hour, the transcription rate of PKC $\beta_1$ in B1/PKC-AZAIIg cells increased five-fold. Smaller increases (two- to three-fold) were also observed in the transcription of the c-jun an c-fos genes in TPA-treated B1/PKC-AZAIIg cells (FIG. 5).

Figure 6:
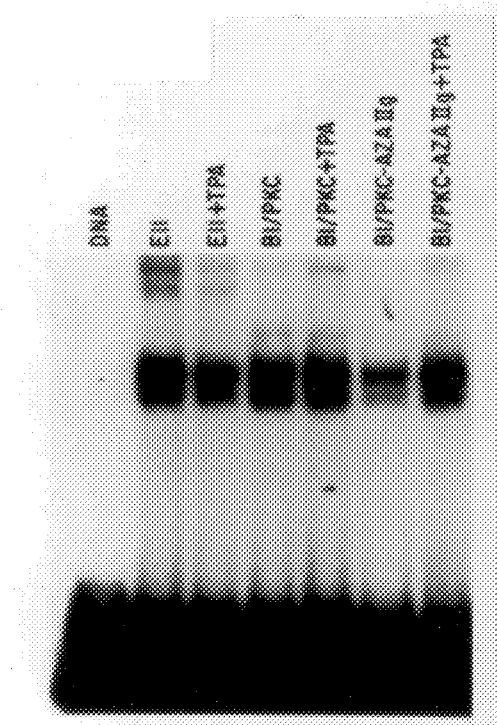
FIGS. 6A–6B Effect of TPA on binding of nuclear proteins from E11, B1/PKC and B1/PKC-AZAIIg to AP-1 and MECA DNA sequences. Gel-shift analysis of complexes formed between an AP-1 oligonucleotide probe (5'-CCAAACAGGATATATGAGTCATGCAGTTC-3') (SEQ. ID NO: 1) (a) or a MECA oligonucleotide probe (5'CCAAACAGGATATCTGTGGTAAGCAGTTCC-3') (SEQ. ID NO: 2) (b) and nuclear extracts prepared from untreated or TPA (24 hours) treated cells. DNA lane refers to the oligonucleotide probe without the addition of nuclear extracts. Addition of a 100-fold excess of the respective competitor DNA sequence in combination with nuclear extracts eliminated binding to the AP-1 and MECA oligonucleotide probes (data not shown).

TPA can induce transcriptional activation of genes containing the palindromic DNA sequence TGACTCA (Seq. ID No. 3), referred to as the TPA-responsive element (TRE) (Lee, et al., 1987; Angel, et al., 1988; Mitchell & Tijian, 1989). The AP-1 multiprotein transcription factor complex, consisting of either c-jun protein homodimers or c-jun/c-fos heterodimers, can bind to the TRE through the leucine zipper dimerization domain resulting in changes in gene expression (Kouzarides & Ziff, 1988; Sasson-Corsi, et al., 1988). Sequence analysis of the Moloney leukemia virus long terminal repeat (LTR), which transcriptionally regulates expression of the PKC $\beta_1$ gene in the pMV7 plasmid, indicated the presence of two tandem AP-1 recognition sites. To determine if the ability of TPA to induce transcriptional increases in the PKC $\beta_1$ gene in B1/PKC-AZAIIg cells involved changes in the level of AP-1 transcription factors applicants isolated nuclear extracts from control and TPA-treated cells and performed DNA-binding (gel retardation) assays. As can be seen in FIG. 6, the level of AP-1 activity in B1/PKC-AZAIIg cells was reduced relative to the levels found in E11 and B1/PKC cells. Following treatment with TPA, the amount of AP-1 activity increased to that observed in B1/PKC cells. In contrast, the level of DNA binding proteins recognizing an enhancer core sequence element (MECA) (Halazonetis, 1992) found in the Moloney leukemia virus LTR was similar in E11, B1/PKC and B1/PKC-AZAIIg cells grown in the presence or absence of TPA. Both AP-1 and MECA binding activities were eliminated by using a 100-fold excess of the respective competitor DNA sequence in combination with nuclear extracts (data not shown).

Figure 7:
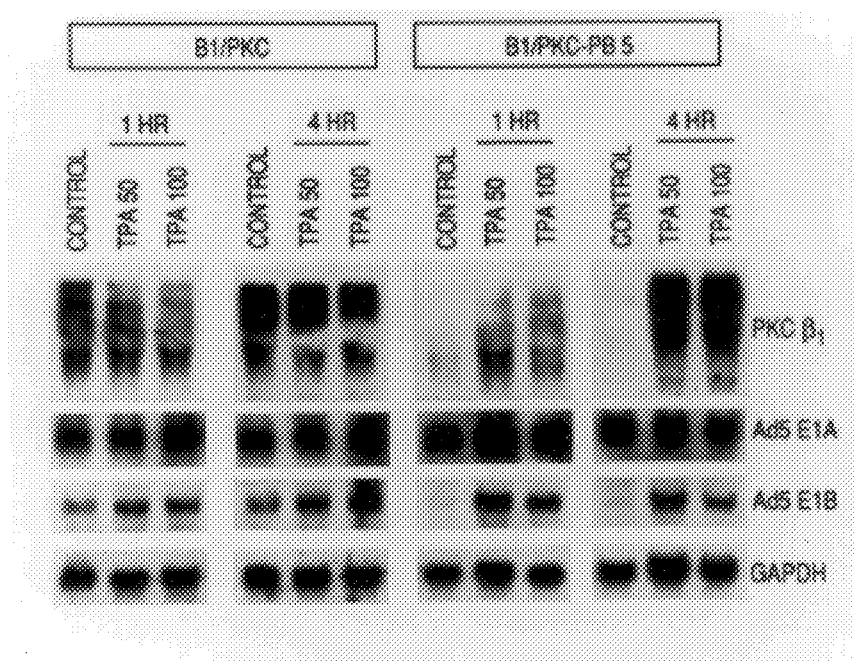
FIG. 7 Effect of TPA on steady state levels of PKC $\beta_1$, Ad5 E1A, Ad5 E1B and GAPDH mRNA in B1/PKC and B1/PKC-PB5 cells. Cells were treated with 50 or 100 ng ml$^{-1}$ for 1 or 4 hours prior to RNA isolation and analysis by Northern hybridization. B1/PKC is a PKC $\beta_1$ expressing subclone. B1/PKC-PB5 is a single-cell subclone of B1/PKC cells treated for 4 days with 4 mM phenylbutyrate and then grown for two weeks in medium lacking PB prior to isolation.

Reversal of the transformation progression phenotype in E11-PKC $\beta_1$ cells by phenylbutyrate (PB) and effect of TPA on gene expression in PB-reverted B1/PKC cells Experiments were also conducted to determine if the demethylating agent PB could induce a suppression in the progression phenotype in PKC $\beta_1$ expressing E11 cells. B1/PKC cells were seeded at clonal cell densities (100, 200 and 400 cells/6 cm plate) treated with 4 mM PB for 4 days and then grown for 2 weeks in medium lacking PB. Colonies were then isolated and grown as independent cell lines in the absence of PB. The B1/PKC-PB 5 clone displayed a reversion of the progression phenotype, i.e., it grew in agar with an efficiency similar to E11 cells. Analysis of gene expression in B1/PKC-PB 5 cells indicated that they no longer synthesized PKC $\beta_1$ or Ad5 E1B mRNA (FIG. 7). As observed with AZA treated B1/PKC cells, treatment with TPA for 1 hour or 4 hours resulted in the induction of PKC $\beta_1$ mRNA expression. In addition, TPA also induced expression of Ad5 E1B mRNA in B1/PKC-PB 5 cells. In contrast, no change in Ad5 E1A or GAPDH expression was observed in B1/PKC or B1/PKC-PB 5 cells grown in the absence or presence of TPA. These observations indicate that PB, like AZA, can reverse the progression phenotype in PKC $\beta_1$ expressing E11 cells and progression suppression is associated with a TPA-reversible inhibition in PKC $\beta_1$ and Ad5 E1B expression.

EXPERIMENTAL DISCUSSION

The Ad5 transformed rat embryo cell culture system is being used to study the contribution of specific genetic and epigenetic changes in the process of transformation progression (Fisher, 1984; Babiss, et al., 1985; Duigou, et al., 1991; Reddy, et al., 1993). Using this model, it has been demonstrated previously that Ad5 transformation is often a multistep process that is profoundly affected by diverse agents, including growth factors, hormones and tumor promoters (reviewed in Fisher, 1984). Using a progressed H5ts125-transformed rat embryo clone, E11-NMT, it has been shown that transformation progression can be reversed, at an efficiency >90%, by a single treatment for 24 hours with AZA (Babiss, et al. 1985). Transformation progression can also be stably suppressed in somatic cell hybrids formed between E11-NMT and non-transformed CREF cells (Duigou, et al., 1990). These results support the hypothesis that transformation progression may be mediated by the expression of an unidentified gene(s) that is regulated by changes in DNA methylation (Babiss, et al., 1985; Duigou, et al., 1991; Reddy, et al., 1993). A basic tenet of applicants' hypothesis is that methylation of the progression suppressor gene(s) results in a loss of expression of this gene and consequently induction of the progression phenotype, whereas demethylation of the putative progression suppressor gene(s) results in gene activation and suppression of the progression phenotype (Babiss, et al., 1985; Duigou, et al., 1991; Reddy, et al., 1993).

The PKC $\beta_1$ gene, which when expressed at low levels can enhance transformation of CREF cells by Ad5 or the Ad5 E1A gene (Su, et al., 1991), induced a progression phenotype in the H5ts125-transformed rat embryo clone, E11. Transformation progression in E11/PKC cells correlated with an increase in both the transcriptional rate and the steady state levels of PKC $\beta_1$ RNA, an increase in PKC enzymatic activity, an increase in [$^3$H]-PDBu binding to cell surface receptors and an increase in anchorage-independence. A single 24 hour treatment with AZA resulted in a reversion of the progression phenotype and a return in the properties of B1/PCK cells to that of the untransfected parental E11 cells (Table 3). As was previously demonstrated in spontaneous progression induced by tumor selection in nude mice (Duigou, et al., 1991), suppression of PKC $\beta_1$-induced progression by AZA in B1/PKC cells did not result in changes in the levels of expression of the Ad5 E1A or E1B transforming genes. Progression suppression by AZA in E11/PKC cells also did not extinguish expression of the neo resistance gene or change expression of the PKC$\epsilon$ or c-jun genes. These observations indicate that transformation progression in E11 cells can be stably induced by expression of a specific PKC isoform, i.e., PKC $\beta_1$, and induction of a putative progression suppressor gene by AZA can nullify this phenotype by selectively altering the expression of specific transformation progression-inducing genes.

Several studies have focused on the effects of over-expression of specific cPKCs on cellular physiology (Housey, et al., 1988; Persons, et al., 1988; Megidish & Mazurek, 1989; Krauss, et al., 1989; Borner, et al., 1991, 1992a, b; Su, et al., 1991, 1992; Watanabe, et al., 1992). Over-expression of PKC $\beta_1$ induced profound changes in cellular phenotype that were dependent on the level of PKC $\beta_1$ expressed and the target cell used (Housey et al., 1988; Krauss, et al., 1989; Choi, et al., 1990; Su, et al., 1991, 1992). When PKC $\beta_1$ was inserted by retroviral vector into CREF, Rat 6 or C3H10T1/2 cells, sublines developed which expressed high levels of PKC $\beta_1$ mRNA, [$^3$H]-PDBu binding and PKC enzymatic activity (Housey, et al., 1988; Krauss, et al., 1989; and Su, et al. 1992). High-level PKC $\beta_1$-expressing CREF cells exhibited a transformed morphology and grew more rapidly in monolayer culture, formed macroscopic colonies in agar in the absence of TPA and in many independent clones TPA further enhanced anchorage-independent growth (Su, et al., 1992). In contrast, insertion of the same PKC $\beta_1$ construct into CREF cells by $Ca^{2+}$-mediated DNA transfection resulted in cultures that displayed a normal CREF-like morphology, exhibited only small changes in [$^3$H]-PDBu binding and PKC enzymatic activity and failed to form macroscopic colonies in agar in the absence or presence of TPA (Su, et al., 1991, 1992). In the case of retroviral PKC $\beta_1$ transformed Rat 6 and C3H10T1/2 cells, high-level PKC $\beta_1$ expressing clones displayed only marginal changes in morphology in the absence of TPA, whereas TPA resulted in profound morphological changes (Housey, et al., 1988; Krauss, et al., 1989). The growth rate and saturation density of high-level expressing PKC $\beta_1$ expressing C3H10T1/2 clones was increased, transformed cells grew in agar in the absence or presence of TPA and transformed cells were tumorigenic in nude mice (Housey, et al., 1988). In contrast, high-level PKC $\beta_1$ expressing C3H10T1/2 clones displayed similar growth rates as control retroviral vector transformed C3H10T1/2 cells and transformed cells did not display anchorage-independent growth and they were not tumorigenic in nude mice (Krauss et al., 1989). Target cell specificity for the action of cPKCs is further indicated by the observation that over-expression of PKC $\beta_1$ in the human HT29 colorectal carcinoma cell line results in growth suppression and an inhibition of oncogenic potential in nude mice (Choi et al., 1990). These studies demonstrate both PKC isoform and cell type specific effects of over-expression of various cPKCs in different target cells.

Over-expression of PKC $\beta_1$ in Rat 6 cells has been shown to alter the expression and TPA regulation of endogenous PKC genes, such as PKC$\delta$ and PKC$\epsilon$ (Borner et al., 1992a). A differential alteration in the regulation of individual PKC isoforms has also been observed in parental Rat 6 (R6) and high-level PKC $\beta_1$ expressing Rat 6 cells (R6-PKC3) transformed with a series of oncogenes, including Ha-ras, src and fos (Borner et al., 1992b). Transformation of R6 or R6-PKC3 cells with an activated c-Ha-ras oncogene resulted in an increase in both the mRNA and protein levels of PKC$\alpha$ and PKC$\delta$, decreased levels of PKC$\epsilon$ mRNA and protein and no change in the expression level of PKC$\zeta$ (Borner, et al., 1992b). The mechanism involved in the enhanced expression of PKC $\alpha$ in c-Ha-ras transformed Rat 6 cells involved an increase in the transcription rate of this PKC gene (Borner et al., 1992b). In contrast, no significant changes in the levels of expression of PKC$\alpha$, PKC$\delta$, PKC$\epsilon$ or PKC$\zeta$ was found in R6 cells transformed by myc, neu/erb-B2 or mos oncogenes (Borner et al., 1992b). In the present study, applicants have determined the effect of over-expression of PKC $\beta_1$ and suppression of PKC $\beta_1$ expression by AZA on the transcriptional rates of various cPKC and nPKC genes. No changes occurred in the transcriptional rates of PKC$\alpha$, PKC$\gamma$ or PKC$\epsilon$ in B1/PKC or B1/PKC-AZAIIg cells (FIG. 5). Similarly, no difference was observed in the mRNA levels of PKC$\epsilon$ in E11, E11-NMT, B1/PKC or B1/PKC AZA cells (FIG. 3). These results suggest that rat embryo cells transformed by Ad5 behave more like myc, neu/erb-B2 or mos oncogene transformed rat cells, than c-Ha-ras transformed rat embryo cells.

The ability of PKC $\beta_1$ to induce transformation progression in E11 cells correlated with the continued expression of this gene, as reflected by increased PKC $\beta_1$ transcriptional rates and mRNA production, enhanced [$^3$H]-PDBu binding and in many instances an increase in PKC enzymatic activity. Induction of expression of the putative transformation progression suppression gene following AZA treatment in B1/PKC-AZAIIg cells was associated with a reduction in all of these PKC-related phenomena. An important question that applicants have begun to investigate is the mechanism by which AZA-treatment induced a suppression in transformation progression in B1/PKC cells. Progression suppression induced by AZA was associated with a decreased level of PKC $\beta_1$ transcription and steady state RNA (FIGS. 3 and 4). Since transcription of the PKC $\beta_1$ gene resulted from transcriptional initiation from a Moloney leukemia virus LTR as opposed to its own endogenous promoter (Perkins et al., 1983; Housey, et al., 1988), the above results suggested the possibility that the induction of the putative progression suppressor gene by AZA might be influencing, either directly or indirectly through positive and/or negative acting cis-regulatory elements, transcription from the Moloney leukemia virus LTR. To begin to dissect the region(s) of the Moloney leukemia virus LTR responsive to AZA suppression studies have been conducted to determine if the binding of transcription factors to sequence specific DNA binding domains are altered following AZA treatment in B1/PKC-AZA cells. A difference was found in the levels of the AP-1 multiprotein transcription factor complex in B1/PKC versus B1/PKC-AZAIIg cells, with the latter cell type displaying less AP-1 activity (FIG. 6). In contrast no consistent changes occurred in AZA treated B1/PKC with respect to the binding of transcription factors interacting with the enhancer core sequence element, MECA, also found in the Moloney leukemia LTR. The level of AP-1 in B1/PKC-AZAIIg returned to that of B1/PKC cells following treatment with TPA. In addition, TPA enhanced transcription and increased steady state RNA levels of the PKC $\beta_1$ and the c-jun gene in B1/PKC-AZAIIg cells. The effect of TPA, however, was transitory and it did not result in a return of the progression phenotype in B1/PKC-AZAIIg cells. These results indicate that AZA can selectively alter the levels of gene expression and transcription regulatory factors in B1/PKC cells. Further studies are necessary to determine if selective modulation of the transcriptional machinery of progressed cells is a component of the mechanism by which AZA induces suppression of the transformation progression phenotype in E11 cells over-expressing PKC $\beta_1$ and/or in spontaneously progressed E11-NMT cells.

In summary, the currently described cell culture model system represents a valuable experimental tool for defining the molecular and biochemical events mediating transformation progression and transformation progression suppression. On the basis of the apparent selective shut-down of transcription from the Moloney leukemia virus LTR following AZA treatment, the present system would also appear amenable for identifying transcriptional regulatory factors that can directly govern expression of genes controlled by LTRs. Further studies designed to address these issues should provide important insights into the molecular determinants of multistage carcinogenesis.

REFERENCES

1. Angel, P., Allegretto, E. A., Okino, S. T., Hattori, K., Boyle, W. J., Hunter, T. & Karin, M. (1988), Nature, 332:166–171.
2. Babiss, L. E., Young, C. S. H., Fisher, P. B. & Ginsberg, H. S. (1983) J. Virol., 46:454–465.
3. Babiss, L. E., Fisher, P. B. & Ginsberg, H. S. (1984). J. Virol., 49:731–740.
4. Babiss, L. E., Zimmer, S. G. & Fisher, P. B. (1985). Science, 228:1090–1101.
5. Bacher, N., Zisman, Y., Berent, E. & Livneh, E. (1991). Mol. Cell. Biol., 11:126–133.
6. Bishop, M. J. (1978). Science, 235:305–311.
7. Bishop, M. J. (1991). Cell, 64:235–248.
8. Borner, C., Eppenberger, U., Wyss, R. & Fabbro, D. (1988). Proc. Natl. Acad. Sci. USA 85:2110–2114.
9. Borner, C., Filipuzzi, L., Weinstein, I. B. & Imber, R. (1991) Nature, 353:78–80.
10. Borner, C., Guadagno, S. N., Fabbro, D. & Weinstein, I. B. (1992a). J. Biol. Chem., 267:12892–12899.
11. Borner, C., Guadagno, S. N., Hsiao, W. W. -L., Fabbro, D., Barr, M. & Weinstein, I. B. (1992b). J. Biol. Chem., 267:12900–12910.
12. Choi, P. M., Tchou-Wang, K. M. & Weinstein, I. B. (1990) Mol. Cell. Biol., 10:4650–4657.
13. Coussens, L., Parker, P., Rhee, L., Yang-Feng, T. L., Waterfield, M. D., Francke, U. & Ullrich, A. (1986) Science, 233:859–866.
14. Dorsch-Hasler, K., Fisher, P. B., Weinstein., I. B. & Ginsberg, H. S. (1980). J. Virol., 34:305–314.
15. Duigou, G. J., Babiss, L. E. & Fisher, P. B. (1989) N.Y. Acad. Sci., 567:302–306.
16. Duigou, G. J., Babiss, L. E., Iman, D. S., Shay, J. W. & Fisher, P. B. (1990) Mol. Cell. Biol., 10:2027–2034.
17. Duigou, G. J., Su, Z.-z., Babiss, L. E., Driscoll, B., Fung, Y.-K. T. & Fisher, P. B. (1991) Oncogene, 6:1813–1824.
18. Eldar, H., Zisman, Y., Ullrich, A. & Livneh, E. (1990) J. Biol. Chem., 265:13290–13296.
19. Fisher, P. B. (1984) Mechanisms of Tumor Promotion. III, Tumor Promotion and Carcinogenesis in vitro, Slaga, T. J. (ed.). CRC Press:Boca Raton, Fla., pp. 57–123.

20. Fisher, P. B., Weinstein, I. B. Eisenberg, D. & Ginsberg, H. S. (1978) Proc. Natl. Acad. Sci. USA, 75:2311–2314.

21. Fisher, P. B., Bozzone, J. H. & Weinstein, I. B. (1979a) Cell, 18:695–705.

22. Fisher, P. B., Dorsch-Hasler, K., Weinstein, I. B. & Ginsberg, H. S. (1979b) Nature, 281:591–594.

23. Fisher, P. B., Goldstein, N. I. & Weinstein, I. B. (1979b) Cancer Res. 39:3051–3057.

24. Fisher, P. B., Babiss, L. E., Weinstein, I. B. & Ginsberg, H. S., (1982), Proc. Natl. Acad. Sci., U.S.A., 79:3527–3531.

25. Friedman, J. M., Babiss, L. E. & Darnell, Jr., J. E., (1986), J. Mol. Biol. 6:3791–3797.

26. Halazonetis, T. D., (1992) Anticancer Res., 12:285–292.

27. Harrington, M. A., Gonzales, F. & Jones, P. A., (1988) Mol. Cell. Biol., 8:4322–4327.

28. Housey, G. M., O'Brian, C. A., Johnson, M. D., Kirschmeier, P. & Weinstein, I. B., (1987), Proc. Natl. Acad. Sci., U.S.A., 84:1065–1069.

29. Housey, G. M., Johnson, M. D., Hsiao, W.-L. W., O'Brian, C. A., Murphy, J. P., Kirschmeier, P. & Weinstein, I. B., (1988), Cell, 52:343–354.

30. Hsiao, W.-L. W., Housey, G. M., Johnson, M. D. & Weinstein, I. B., (1989), Mol. Cell. Biol., 9:2641–2647.

31. Jiang, H., Waxman, S. & Fisher, P. B., (1993), Mol. Cell. Different., 1(2):197–214.

32. Jones, P. A., (1985), Cell, 40:485–486.

33. Knopf, J. L., Lee, M.-H., Sultzman, L. A., Kriz, R. W., Loomis, C. R., Hewick, R. M. & Bell, R. M., (1986), Cell, 46:491–502.

34. Kouzarides, T. & Ziff, E. (1988), Nature, 336:646–651.

35. Krauss, R. A., Housey, G. M., Johnson, M. D. & Weinstein, I. B., (1989), Oncogene, 4:991–998.

36. Lee, W., Mitchell, P. & Tijian, R., (1987), Cell, 49:741–752.

37. Liang, P. and Pardee, A. B. (1992) Science, 257:967–971.

38. Marshall, C. J. (1991), Cell, 64:313–326.

39. Megidish, T., & Mazurek, N. (1989), Nature, 342:807–811.

40. Mischak, H., Goodnight, J., Kolch, W., Martiny-Baron, G., Schaechtle, C., Kanietza, M. G., Blumberg, P. M., Pierce, J. H. & Mushinski, J. F. (1993), J. Biol. Chem., 268:6090–6096.

41. Mitchell, P. J. & Tijian, R., (1989), Science, 245:249–251.

42. Nicholson, G. L., (1987), Cancer Res. 47:1473–1487.

43. Nishizuka, Y., (1988), Nature, 334:661–665.

44. Nishizuka, Y., (1992), Science, 258:607–614.

45. Nowell, P. C., (1986), Cancer Res., 46:2203–2207.

46. O'Brian, C. A., Fan, D., Ward, N. E., Seid, C. & Fidler, I. J., (1989), FEBS Lett., 246:78–82.

47. Ohno, S., Akita, Y., Konno, Y., Imajoh, S. & Suzuki, K., (1988), Cell, 53:731–741.

48. Ohno, S., Akita, Y., Hata, A., Osada, S., Kubo, K., Konno, Y., Akimoto, K., Mizuno, K., Saido, T., Kuroki, T. & Suzuki, K., (1991), Adv. Enzyme Reg. 31:287–303.

49. Ono, Y., Kurokawa, T., Kawahara, K., Nishimura, O. Marumoto, R., Igarashi, K., Sugiro, Y., Kikkawa, Y., Ogita, K. & Nishizuka, Y., (1986), FEBS Lett., 203:111–115.

50. Ono, Y., Fujii, T., Ogita, K., Kikkawa, U., Igarashi, K., & Nishizuka, Y., (1988), J. Biol. Chem., 263:6927–6932.

51. Osada, S., Mizuno, K., Saido, T. C., Akita, Y., Suzuki, K., Kuroki, T. & Ohno, S., (1990), J. Biol. Chem., 265:22434–22440.

52. Parker, P. J., Coussens, L., Totty, N., Rhee, L., Young, S., Chen, E., Waterfield, M. D., Francke, U. & Ullrich, A., (1986), Science, 233:853–859.

53. Perkins, A. S., Kirschmeier, P. T., Gattoni-Celli, S. & Weinstein, I. B., (1983), Mol. Cell. Biol., 3:1123–1132.

54. Persons, D. A., Wilkison, W. O., Bell, R. M. & Finn, O. J., (1988), Cell, 52:447–458.

55. Reddy, P. G., Su, Z.-z & Fisher, P. B., (1993), Chromosome and Genetic Analysis. Methods in Molecular Genetics Adolph, D. W. (ed). Academic Press, Orlando, Florida., Vol. I, pp. 68–102.

56. Sager, R. (1989), Science, 246:1406–1411.

57. Sager, R. Anisowicz, A., Neveu, M., Liang, P. and Sotiropoulou, G. (1993) FASEB, 7:964–970.

58. Sassone-Corsi, P., Ransome, L. J., Lamph, W. W. & Verma, I. M., (1988), Nature, 336:692–695.

59. Scott, R. E., Estervig, D. N., Tzen, C. Y., Minoo, P., Maercklein, P. B. & Hoerl, B. J., (1989), Proc. Natl. Acad. Sci. U.S.A., 86:1652–1656.

60. Su, Z.-z. & Fisher, P. B., (1992), Poly ADP-Ribosylation Reactions. Poirier, G. L. & Moreau, P. (eds.). Springer-Verlag, New York, pp. 203–210.

61. Su, Z.-z, Zhang, P. & Fisher, P. B., (1990), Mol. Carcinogenesis, 3:309–318.

62. Su, Z.-z., Duigou, G. J. & Fisher, P. B., (1991), Mol Carcinogenesis, 4:328–337.

63. Su, Z.-z., O'Brian, C. A. & Fisher, P. B., (1992), Cell. Mol. Biol., 38:27–39.

64. Su, Z.-z., Austin, V. N, Zimmer, S. G. & Fisher, P. B., (1993), Oncogene, 8:1211–1219.

65. Sun, Y., Hegamyer, G., and Colburn, N. H., (1994), Cancer Res. 54:1139–1144.

66. Taylor, S. M. & Jones, P. A., (1979), Cell, 17:771–779.

67. Ward, N. E. & O'Brian, C. A., (1992), Biochemistry, 31:5905–5911.

68. Watanabe, T., Ono, Y., Taniyama, Y., Hazama, K., Igarashi, K., Ogita, K., Kikkawa, U. & Nishizuka, Y., (1992), Proc. Natl. Acad., Sci., U.S.A., 89:10159–10163.

69. Weinberg, R. S., (1985), Science, 230:770–776.

70. Weinstein, I. B., (1988), Cancer Res., 48:4135–4143.

What is claimed is:

1. A method of isolating a progression suppressor gene which suppresses expression of a gene regulated by a long terminal repeat of a Moloney leukemia virus comprising:
   a) introducing DNA containing the long terminal repeat regulated protein kinase C $B_1$ gene of pMV7-PKC into a population of Ad5-transformed cells, E11 Cells;
   b) treating the cells resulting from step (a) with a DNA demethylating agent so as to induce the expression of at least one progression suppressor gene and thereby cause a subpopulation of the cells to selectively suppress the expression of the long terminal repeat regulated protein kinase C $B_1$ gene;
   c) selecting cells resulting from step (b) which express the progression suppressor gene;
   d) isolating mRNA from the cells resulting from step (c);
   e) comparing the mRNA so obtained with mRNA obtained from uninduced transformed cells so as to identify mRNA only expressed by the cells resulting from step (c); and
   f) isolating the gene encoding the mRNA identified in step e) so as to thereby identify the progression suppressor gene.

2. The method of claim 1, where in step b) the cells are treated with 5-azacytidine or phenyl butyrate.

3. The method of claim 1, where in step f) the progression suppressor gene is isolated by subtractive hybridization or differential display.

4. A method of isolating a gene which inhibits the expression of a gene regulated by a long terminal repeat of a Moloney leukemia virus comprising:
   a) introducing DNA containing the long terminal repeat regulated protein kinase C $B_1$ gene of pMV7-PKC into a population of Ad5-transformed cells, E11 cells;
   b) treating the cells resulting from step (a) with a DNA demethylating agent so as to induce the expression of at least one progression suppressor gene and thereby suppress expression of the long terminal repeat regulated protein kinase C $B_1$ gene; and
   c) isolating the gene which inhibits the function of the long terminal repeat.

5. The method of claim 4, where in step c) the gene is isolated by subtractive hybridization or differential display.

6. A method of isolating a gene which activates the expression of a gene regulated by a long terminal repeat of a Moloney leukemia virus comprising:
   a) introducing DNA containing the long terminal repeat regulated protein kinase C $B_1$ gene of pMV7-PKC into a population of Ad5-transformed cells, E11 cells;
   b) treating the cells resulting from step (a) with a DNA demethylating agent so as to induce the expression of at least one progression suppressor gene and thereby suppress expression of the long terminal report regulated protein kinase C $B_1$ gene;

c) treating the cells resulting from step b) with an amount of protein kinase C activating compound or an inhibitor of serine or threonine specific protein phosphatase effective to activate the expression of the gene regulated by the long terminal repeat; and d) isolating the gene which activates the expression of the gene regulated by the long terminal repeat.

7. The method of claim 6 wherein the protein kinase C activating compound is a tumor promoting diterpene phorbol ester.

8. The method of claim 6 wherein the protein kinase C activating compound is a synthetic protein kinase C activator.

9. The method of claim 8, wherein the activator is 3-(N-acetylamino)-5-(N-decyl-N-decyl-N-methylamino) benzyl alcohol or 6-(N-decylamino)-4-hydroxymethylindole.

10. The method of claim 6 wherein the inhibitor is calyculin or okadaic acid.

11. The method of claim 6, where in step d) the gene is isolated by subtractive hybridization or differential display.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (xi) SEQUENCE DESCRIPTION: SEQ ID NO:1:

CCAAACAGGA TATATGAGTC ATGCAGTTC                                29

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:2:

CCAAACAGGA TATCTGTGGT AAGCAGTTCC                               30

(2) INFORMATION FOR SEQ ID NO:3:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:3:

TGACTCA                                                        7